US006803020B1

(12) United States Patent
Agnely et al.

(10) Patent No.: US 6,803,020 B1
(45) Date of Patent: Oct. 12, 2004

(54) METHOD FOR PREPARING LATEX BY EMULSION (CO) POLYMERIZATION OF ETHYLENICALLY UNSATURATED MONOMERS, WITH DIRECT INLINE MONITORING BY RAMAN SPECTROSCOPY

(75) Inventors: Mathias Agnely, Paris (FR); Bruno Amram, Ivry-sur-Seine (FR); Phil D. Armitage, Bradford (GB); Dominique Charmot, Los Gatos, CA (US); Bruno Drochon, Noisy-le-Grand (FR); Eve Pere, Lons (FR)

(73) Assignee: Raisio Chemicals OY, Raisio (FI)

( * ) Notice: Subject to any disclaimer, the term of this patent is extended or adjusted under 35 U.S.C. 154(b) by 0 days.

(21) Appl. No.: 09/913,838

(22) PCT Filed: Feb. 14, 2000

(86) PCT No.: PCT/FR00/00360

§ 371 (c)(1),
(2), (4) Date: Jan. 7, 2002

(87) PCT Pub. No.: WO00/49395

PCT Pub. Date: Aug. 24, 2000

(30) Foreign Application Priority Data

Feb. 18, 1999 (FR) .............................. 99 02011

(51) Int. Cl.$^7$ ........................... G01N 21/65; C08F 2/22; C08L 25/00; C08L 25/10
(52) U.S. Cl. ..................... 422/82.11; 524/804; 524/836
(58) Field of Search ................................ 524/836, 804; 422/82.11

(56) References Cited

U.S. PATENT DOCUMENTS

| 4,613,649 | A | * | 9/1986 | Saeki et al. ................. 524/650 |
| 4,802,761 | A | * | 2/1989 | Bowen et al. ............... 356/301 |
| 4,802,984 | A | * | 2/1989 | Waite ......................... 210/490 |
| 5,312,847 | A | * | 5/1994 | de Vos ........................ 521/137 |
| 6,175,409 | B1 | * | 1/2001 | Nielsen et al. .............. 356/337 |

FOREIGN PATENT DOCUMENTS

EP        0 567 214 A    10/1993

OTHER PUBLICATIONS

Feng L and Ng K.Y.S., "Characterization of Styrene Polymerization in Microemulsion by Raman Spectrosocpy", *Colloids and Suraces*, 1991, pp. 349–361, vol. 53, No. 3–4; XP002120792 abstract pp. 351–355.

Claybourn M et al, "Analysis of Processes in Latex Systems by Fourier Transform Raman Spectroscopy", *Journal of Raman Spectroscopy*, 1994, pp. 123–129, vol. 25; XP002069189 abstract, p. 123.

Chang S.Y. and Nam S.W., "Monitoring Polymerization Reactions by Near–IR Spectroscopy", *Acs Symposium Series: Multideminsional Spectroscopy of Polymers*, pp. 147–165, XP002120793 pp. 153–159.

Vivarat–Perrin, M.P.; "Le Spectrometre Raman S'Installe En Ligne A 200 M Des Capteurs", *Mesures Regulation Automatisme*, Apr. 1, 1998, pp. 63–66, No. 704; XP000780554, p. 66.

Adar F et al, "Raman Spectroscopy for Process/Quality Control", *Applied Spectroscopy Reviews*, 1997, pp. 45–101, vol. 32, No. 1/02; XP000695107, ISSN: 0570–4928, p. 58, p. 77.

Sawatzki J., "FT–Raman–Spektroskopie in–line", *CLB Chemie in Labor und Biotechnik*, 1999, pp. 33–335, vol. 50, No. 9; XP002120794.

* cited by examiner

*Primary Examiner*—Tae H Yoon
(74) *Attorney, Agent, or Firm*—Burns, Doane, Swecker & Mathis, L.L.P.

(57) ABSTRACT

The invention concerns a novel method for preparing latex by emulsion (co)polymerization of ethylenically unsaturated monomers, wherein the direct inline monitoring is carried out by Raman spectroscopy. The invention also concerns latex compositions obtainable by the emulsion (co) ploymerization method whereof the direct inline monitoring is performed by Raman spectroscopy. The invention further concerns a device for implementing said method, said device comprising a reactor, at least an optical probe, a Raman spectrometer, optical fibers, a computer and a regulating automaton.

8 Claims, 9 Drawing Sheets

METHOD FOR PREPARING LATEX BY EMULSION (CO) POLYMERIZATION OF ETHYLENICALLY UNSATURATED MONOMERS, WITH DIRECT INLINE MONITORING BY RAMAN SPECTROSCOPY

A subject matter of the present invention is a novel process for the preparation of a latex by emulsion (co) polymerization of ethylenically unsaturated monomers, in which the direct in-line monitoring of the (co) polymerization is carried out by Raman spectroscopy.

The latex-based compositions capable of being obtained by the emulsion (co)polymerization process, the in-line monitoring of which is carried out by Raman spectroscopy, constitute the second subject matter of the invention.

Finally, the third subject matter of the invention relates to a device for the implementation of the abovementioned process, this device comprising a reactor, at least one optical probe, a Raman spectrometer, optical fibers, a calculator and an adjusting automaton.

Latex-based compositions are used in numerous industries, in particular in those of paints, coatings, adhesives, textiles and paper coating. Among latex preparation processes, emulsion (co)polymerization is the most commonly used process.

The properties of the latex-forming (co)polymer are closely related to its overall chemical composition but also to its macromolecular characteristics, such as the microstructure of the chains, the heterogeneity of their chemical composition, their molecular mass distribution and the fraction of optionally crosslinked (co)polymer. The necessary and desired properties are, of course, different according to the field of application of the latices. By way of examples, the desired properties are, for the coating of paper, the dry pick resistance, the wet pick resistance and the wrinkle resistance of the coated papers, for the coating of carpets, including fitted carpets, the mechanical strength and the flexibility, for adhesives, the adhesiveness and the shear strength, and for paints, the wet abrasion resistance, the blocking resistance and the film-forming temperature.

It is thus important to be able to employ a process for preparing a latex which makes it possible to obtain the latter with an overall chemical composition predefined in advance but also with predefined characteristics, in order to provide for and anticipate its future use in a field of application.

For this reason, the reproducibility of the process from one operation to another (batch to batch) is a key element in guaranteeing a consistent level of performance of the latex to the user of the latter. The reproducibility of the process and the consistent quality of the latex obtained are guaranteed by following the process instructions and by identifying the critical parameters of the latter; use may be made, for this, of a methodology, such as Statistical Process Control. In order for this to be all the more effective, it is necessary to be able to have available relevant indicators of the polymerization and preferably indicators which can be measured during the process and not after the process, so as to be able to correct situations of drift. There thus exists a need to have available a technique for the in-line monitoring of the polymerization.

It is known to define the reaction parameters of a process for the preparation of a latex by (co)polymerization in intending to obtain a latex with the appropriate properties in comparison with its use: for example, by defining the temperature profiles and the addition of the reactants, such as the monomers, during the reaction. These reaction parameters thus defined generally result in a (co)polymerization rate profile which condition the characteristics of the latex obtained.

However, it is apparent that, at the industrial level, observing the process parameters (temperature, feed profile of the monomers, pressure, and the like) does not guarantee absolute reproducibility of said process and thus the production of a latex with predefined and appropriate qualities in comparison with their future use. This is because the reaction rate profile can be affected by other factors, such as the impurities present in the reactants [water, monomer(s), surfactant(s), and the like], the fluctuation in stirring rate, the surface condition of the reactant, the fluctuation in size of the particles, and the like.

Given the great economic and industrial stake with regard to the latices, there is very great advantage in having available an optimized emulsion (co)polymerization process for their preparation which guarantees to the user, above all, a consistent level of performance conferred by latices with predefined properties. Such a process must thus exhibit improved reproducibility.

To these ends, there has now been developed, and it is this which constitutes the first subject matter of the present invention, a novel optimized process for the preparation of a latex which exhibits improved reproducibility and, in addition, which is easy to implement, which has an acceptable manufacturing cost and which can be used on an industrial scale. This preparation process by emulsion (co) polymerization of at least one kind of ethylenically unsaturated monomer is carried out by continuous in situ monitoring of the (co)polymerization comprising the following stages:

(i) incident light radiation within the spectral band situated between 200 nm and 1 400 nm, and preferably between 700 nm and 1 400 nm, is emitted into the emulsion, (ii) the light scattered by the reaction medium is picked up and transmitted to a Raman spectrometer, (iii) the Raman spectrum, which shows the energy of the scattered light as a function of the difference in wavelength with respect to the incident light radiation, is determined, (iv)
  a) either the intensities (areas or heights) of specific lines of the spectrum:
    of un(co)polymerized free monomer(s) in the reaction medium,
    and of the polymer obtained;
  b) or the concentrations of un(co)polymerized free monomer(s) in the reaction medium and of the polymer obtained are calculated from the Raman spectrum using quantitative spectral analytical methods, these methods preferably being multivariable chemometric methods;

(v) the process data are subsequently calculated either from the concentrations of free monomer(s) and of the polymer obtained or from the intensities (areas or heights) of specific lines of the spectrum of free monomer(s) in the reaction medium and of the polymer obtained;

(vi) these process data are compared with reference data specific to the process for the production of the latex with the predefined properties;

(vii) and the reaction parameters, such as the temperature, the pressure, the stirring of the medium and the feeding with monomers, are adjusted in order to minimize the difference between the process data measured in-line and the reference process data.

In the context of the present invention, the Raman spectrometer can be a Fourier transform Raman spectrometer or an optical dispersive Raman spectrometer. According to a particular advantageous form, the spectrometer is a Fourier transform Raman (FT-Raman) spectrometer.

One of the advantageous characteristics of the process according to the invention is in particular its continuous implementation, requiring no withdrawal and/or preparation of sample beforehand.

A second advantageous characteristic of the process according to the invention is the minimization of its sensitivity to possible local absences of homogeneity in the medium within the reactor; this being due mainly to the simultaneous determination of the intensities of lines or of the concentrations of free monomer(s) and of the polymer obtained.

A third advantageous characteristic of the invention is the complete suitability of the process according to the invention for direct in-line monitoring carried out in situ.

BRIEF DESCRIPTION OF FIGURES OF DRAWINGS

Figure 1:
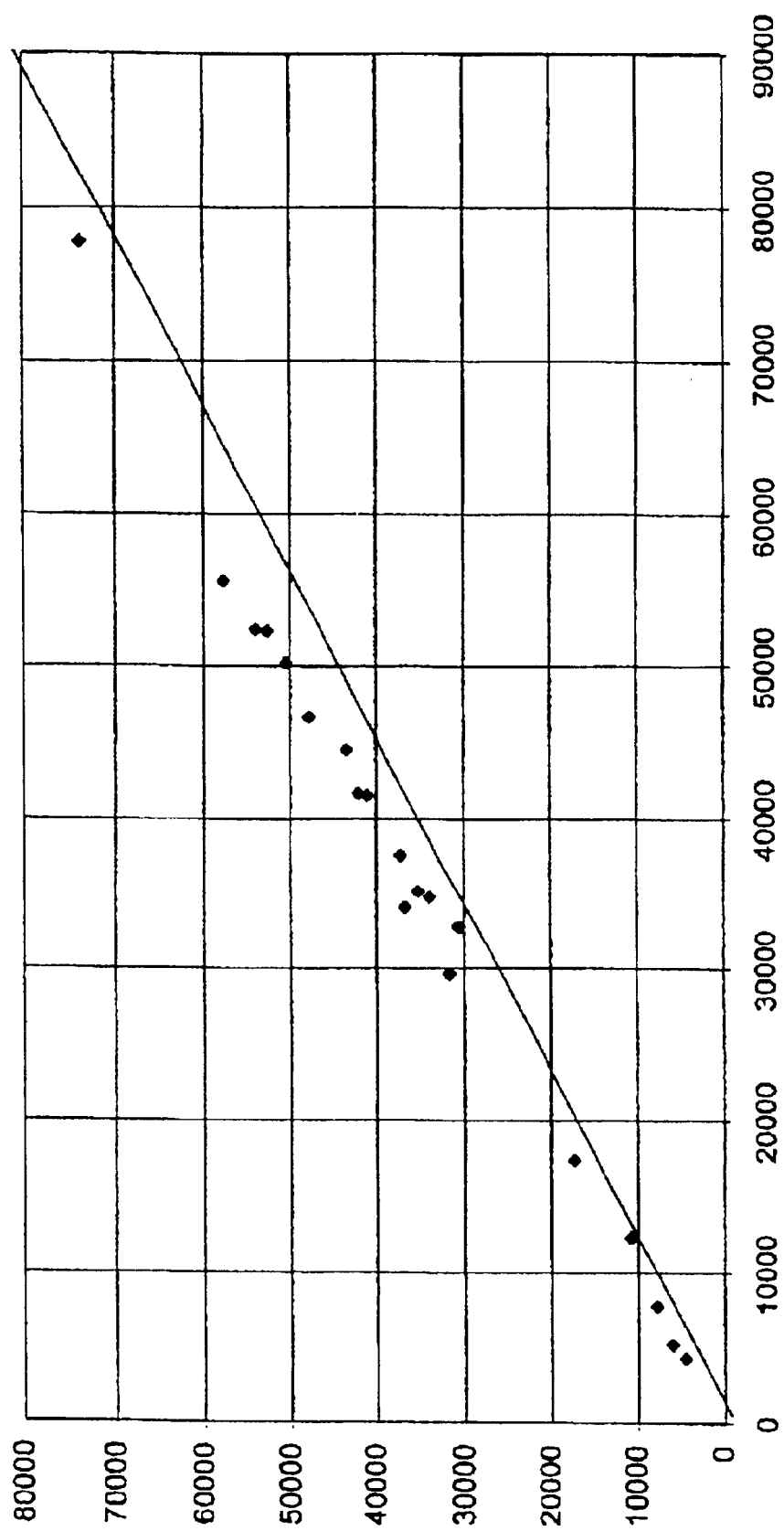
FIG. 1 is a graph showing actual and predicted styrene concentrations during the polymerization in Example 1.

The term "in-line monitoring" is understood to mean not only the direct in-line analysis of the (co)polymerization by recovery of process data calculated in real time and defined from the Raman spectra but also the in-line adjustment, that is to say the adjustment of the reaction parameters according to the calculated data in order to optimize the process in order to obtain a latex with predetermined qualities appropriate for its future use.

More specifically, for a given latex which it is desired to obtain, this adjustment takes place in order to reduce the difference between the process data and reference data to a minimum and preferably to a value close to zero, these reference data being determined beforehand and corresponding to those which are observed in the case where the process is optimized for the preparation of said latex with predetermined and desired qualities. For this, the reference data are selected from experimental trials resulting in the latices with the desired properties. These reference data are determined by measurement on withdrawn samples in off-line analysis or preferably in on-line analysis. These reference data subsequently make possible the establishment of a reference curve for said latex.

In other words, the direct in-line monitoring of the emulsion (co)polymerization by Raman spectroscopy reflects, first, through the spectra processed and converted into process data, the state of progress of the (co)polymerization at any instant. Then, secondly, simultaneously or virtually simultaneously, the direct in-line monitoring of the (co)polymerization by Raman spectroscopy makes possible the adjustment of the reaction parameters of the (co)polymerization process. Thus, the in-line monitoring makes it possible to improve the reproducibility of the (co) polymerization processes and to obtain latices with properties which are predetermined according to the desired objective.

The calculations of the process data and reference data can be made according to various methods. By way of example, the process data mentioned below can be monitored as a function of time:

(a) the intensities of specific lines of the Raman spectrum (areas or heights) of the monomer(s) and of the polymer, (b) the concentration of monomer $Cm$ and the concentration of polymer $Cp$, (c) the ratio of the intensities of specific Raman lines (areas or heights) of the monomer(s) to the intensities of specific Raman lines (areas or heights) of the polymer.

(d) the ratio of the monomer concentration to the polymer concentration $Cm/Cp$, (e) the instantaneous conversion, defined by $Xi=Cp/(Cp+Cm)$, (f) the cumulative conversion, defined by $Xc=Cp \times Vtot/Mtot$, where $Vtot$ is the reaction volume of the latex and $Mtot$ is the total monomer mass involved in the process.

The units of these data are not important; however, they must be consistent with one another.

According to a preferred alternative form of the invention, the process data which make possible the establishment of the reference curve are based on the instantaneous conversion $Xi$ and the cumulative conversion $Xc$.

The reference data $Xi^0$ and $Xc^0$, represented in the form of a curve $Xi^0=F(Xc^0)$, are thus first obtained from trials which have resulted in the characteristics desired for the purpose of the future application. In subsequent trials forming the subject of the direct in-line monitoring, the values of $Xi$ and of $Xc$ obtained in real time are compared with the reference curve.

When a difference is observed between the calculated data $Xi$ and $Xc$ resulting from the process and the reference data $Xi^0$ and $Xc^0$, adjustment is carried out by corrective actions on the process reaction parameters in order to minimize this difference and, for this reason, to provide better reproducibility of said process for a given latex.

By way of example, in order to quantify the increase in reproducibility contributed by the in-line control of the polymerization, it is possible to measure the dispersion index (DI), which determines the difference of the process data $Xi$ and $Xc$ and the reference data $Xi^0$ and $Xc^0$ for a series of polymerization trials. This dispersion index, which characterizes the variability of the process, will be calculated by analyzing the data according to well known statistical methods, as described in Draper N. R., Smith H., 'Applied Regression Analysis', Second Edition, Wiley, 1981; Bates D. M., Watts D. G., 'Nonlinear Regression Analysis and its Applications', Wiley, 1988; and Tomassone R., Lesquoy E., Miller C., "La Regression, Nouveaux Regards sur une Ancienne Methode Statistique" [Regression, a New Look at a Long-Established Statistical Method], Masson, 1983.

The term "(co)polymerization" is understood to denote, for the purposes of the present invention, both the homopolymerization of ethylenically unsaturated monomers and their copolymerization.

Emulsion (co)polymerization denotes any emulsion (co) polymerization process known to a person skilled in the art involving monomers as defined below in the presence of emulsifying agents and (co)polymerization initiators.

The nature of the emulsifying agents and initiators is not critical. The process according to the invention applies to any process for the emulsion (co)polymerization of ethylenically unsaturated monomers in the presence of the usual initiators and emulsifying agents for these types of (co) polymerization.

As regards the quantitative spectral analytical methods, they make it possible to measure the intensities (areas or heights) of specific lines of the spectrum or to determine the concentrations of monomer(s) and of the polymer, preferably by using multivariable chemometric methods.

For the direct intensity measurements on lines of the Raman spectrum, it is possible, by way of examples, to measure the following respective areas or heights:

on the one hand, at approximately $1\ 635 \pm 100\ cm^{-1}$, a line associated with the stretching vibration of the carbon-carbon double bond of the free monomers which have not yet (co)polymerized, and, on the other hand, at approximately $1\ 660 \pm 100\ cm^{-1}$, a line associated with the stretching vibrations of the carbon-carbon double bonds incorporated in the main chain of the polymer when the monomer mixture comprises at least one diene compound.

The term "multivariable chemometric methods" is understood to mean the multivariable analytical techniques known to a person skilled in the art, such as:

the partial least squares technique, the "neuronal network" analytical technique.

Reference may in particular be made on this subject to the document "Partial Least Squares Methods for Spectral Analyses" by Haaland D. M. and Thomas E. V., Anal. Chem., 1988, 60, 1193.

According to an advantageous alternative form of the invention, the direct in-line monitoring is carried out by calculating the concentrations of free monomer(s) and of the polymer obtained by multivariable chemometric analytical methods, this calculation being made by a computer having in memory equations establishing a correlation between the Raman spectra and the concentrations of free monomer(s) and of the polymer obtained and the measured Raman spectra being introduced into said memory in order to calculate the concentrations of free monomer(s) and of the polymer obtained during the polymerization.

In general, the frequency of the measurements recorded is tailored according to the rate of change of the process data. For example, the recordings are made at intervals of between 1 second and 30 minutes and preferably between 10 seconds and 10 minutes.

Use is generally made, as ethylenically unsaturated monomers, of the monomers chosen from the group consisting:

of styrene and/or its derivatives, in particular derivatives such as α-methylstyrene or vinyltoluene;

of dienes, such as butadiene, isoprene or 2-chloro-1,3-butadiene;

of (meth)acrylic esters, this term denoting esters of acrylic acid and of methacrylic acid with hydrogenated or fluorinated $C_1$–$C_{12}$, preferably $C_1$–$C_8$, alcohols, in particular methyl acrylate, ethyl acrylate, propyl acrylate, n-butyl acrylate, isobutyl acrylate, 2-ethylhexyl acrylate, tert-butyl acrylate, methyl methacrylate, ethyl methacrylate, n-butyl methacrylate or isobutyl methacrylate;

of vinyl nitriles, preferably those having from 3 to 12 carbon atoms, such as acrylonitrile and methacrylonitrile;

of carboxylic acid vinyl esters, such as vinyl acetate, vinyl versatate or vinyl propionate;

of vinyl halides;

and their mixture.

Other ethylenically unsaturated monomers, alone or as mixtures, (co)polymerizable with the above monomers are chosen from the group consisting of:

unsaturated ethylenic mono- and dicarboxylic acids, such as acrylic acid, methacrylic acid, itaconic acid, maleic acid or fumaric acid;

monoalkyl esters of the abovementioned dicarboxylic acids with alkanols, preferably having from 1 to 4 carbon atoms, and their N-substituted derivatives;

amides of unsaturated carboxylic acids, such as acrylamide, methacrylamide, N-methylolacrylamide, methacrylamide and N-alkylacrylamides;

ethylenic monomers comprising a sulfonic acid group and its alkali metal or ammonium salts, such as vinylsulfonic acid, vinylbenzenesulfonic acid, α-acrylamidomethylpropanesulfonic acid or 2-sulfoethylene methacrylate;

unsaturated ethylenic monomers comprising a secondary, tertiary or quaternary amino group or a heterocyclic group comprising nitrogen, such as, for example, vinylpyridines, vinylimidazole, aminoalkyl (meth) acrylates and aminoalkyl(meth)acrylamides, such as dimethylaminoethyl acrylate or dimethylaminoethyl methacrylate, di(tert-butyl)aminoethyl acrylate or di(tert-butyl)aminoethyl methacrylate or dimethylaminomethylacrylamide or dimethylaminomethylmethacrylamide;

zwitterionic monomers, such as sulfopropyl(dimethyl) aminopropyl acrylate;

and their mixture.

According to an advantageous alternative form of the invention, the direct in-line monitoring is carried out by Fourier transform Raman spectroscopy and relates to the aqueous emulsion (co)polymerization of styrene and butadiene for the preparation of a latex of styrene-butadiene type.

The invention also relates to a device for the direct in-line monitoring in situ of the process for the preparation of a latex with predefined properties by emulsion (co) polymerization of ethylenically unsaturated monomers. This device according to the invention comprises:

(i) a reactor comprising at least one means for feeding with monomers, with surfactants, with (co) polymerization initiator and with water;

(ii) at least one optical probe which makes it possible to analyze the contents of the reactor;

(iii) a Raman spectrometer;

(iv) at least one optical fiber via which fiber incident light radiation with a wavelength of between 200 nm and 1 400 nm, and preferably between 700 nm and 1 400 nm, is conveyed from the Raman spectrometer to the optical probe, and via which fiber the light scattered by the reaction medium is reconveyed to the spectrometer providing the Raman spectrum, the optical fiber being identical or different for the conveying and the reconveying;

(v) a calculator, coupled to the spectrometer, using quantitative spectral analytical methods making it possible to calculate, from the Raman spectrum:

a) either the intensities (areas or heights) of specific lines of the spectrum of un(co)polymerized free monomer(s) in the reaction medium and of the polymer obtained, b) or the concentrations of un(co)polymerized free monomer(s) in the reaction medium and of the polymer obtained, from the Raman spectrum using quantitative spectral analytical methods, these methods preferably being multivariable chemometric methods;

(vi) and an adjusting automaton in which is programmed at least one mathematical algorithm making it possible to adjust the reaction parameters, such as the temperature, the pressure, the rate of stirring of the medium and the feeding with monomers, in order to minimize the difference between the process data measured in-line and the reference process data; the process data being based on an algebraic transformation either of the line intensities or of the concentrations of free monomer(s) and of the polymer obtained, and the reference data, based on this same algebraic transformation, being specific data of the process for the production of the latex with predefined properties.

The Raman spectrometer used is preferably a Fourier transform spectrometer (FT-Raman) and comprises a source of light radiation, an interferometric optical system, a detector, an electronic system and a computing system.

This spectrometer makes it possible to obtain Raman spectra which give the intensity of the scattered light as a function of the difference in wavelength with respect to the incident radiation.

More specifically, the Fourier transform spectrometer advantageously comprises:

a source of light radiation intended to bring about light scattering by photon excitation of the molecules, an interferometric optical system which is used, inter alia, to screen out the Rayleigh scattering and to modulate the scatter signal, which modulation is carried out by virtue of the establishment of interferences between light radiation with two different values, a detector which converts light energy into electrical energy, an electronic system, the function of which is, inter alia, to convert the analog signal into a digital signal which can be used by the computing system, and a data processing system which is used, inter alia, to control the spectrometer, to carry out the data acquisition and to carry out the data processing, including in particular the inverse Fourier transform which provides the Raman spectrum.

The calculator, coupled to the spectrometer, carries out data processing employing measurements of the intensity (area or height) of certain specific lines of the Raman scattering spectrum or a chemometric analysis, preferably a multivariable chemometric analysis. This chemometric analysis makes it possible to determine both the concentrations of monomer(s) present and of the polymer. In the latter case, the calculator has in memory the equations establishing a correlation between the Raman spectra obtained and the chemical composition of the latex in the course of polymerization. Thus, the measured Raman spectra are introduced into said memory and the chemical composition of the latex in the course of polymerization is then calculated.

The calculator and the computing system of the Raman spectrometer can form two different and separate entities or a single entity.

The source of light radiation used for the incident irradiation is monochromatic. It is preferably a laser. Mention may be made, as examples of possible lasers, of an ionized argon laser (514.5 nm) or advantageously an Nd:YAG laser (1 064 nm). Generally, the source of light radiation emits irradiation with a wavelength of between 200 nm and 1 400 nm, and preferably between 700 nm and 1 400 nm.

The optical probes for the analysis of the contents of the reactor can be found commercially. Mention will be made, by way of example, of the Ramprobe probe from Bruker Optik (Germany). The analytical optical probe is directly positioned close to the reactor, without distinction either in contact with the reaction medium or placed behind a window, so that there is no physical contact between said probe and the reaction medium.

However, it is recommended for the optical probe to be positioned so that it is immersed from the beginning of the polymerization; under these conditions, the monitoring measurements made are representative of the process under way.

The optical probe positioned in the reactor is capable of withstanding the high pressures developed during polymerization and the negative pressures applied before polymerization for the purpose of removing oxygen from the reactor. In addition, the probe must be completely leaktight in order to exclude any escape of gaseous monomer.

Furthermore, the optical probe preferably comprises one or more means intended to weaken and/or to remove the interfering spectrum or spectra. These means are in particular a first means intended to remove the Raman spectrum produced by the optical fiber transporting the incident irradiation and a second means intended to weaken the Rayleigh scattering of the probed molecules. In general, these means are optical filters chosen in particular from holographic filters, dielectric filters and dichroic filters.

The adjusting automaton is a programable device composed of at least one adjusting mathematic algorithm, said device being in contact with the calculator coupled to the Raman spectrometer, makes it possible to act continuously on the parameters of the process to preferably reproduce a predetermined instantaneous conversion profile.

Mention may be made, as examples of optical fibers which can be used in the context of the invention, of the fibers from CIC Photonics Inc., USA, from C Technologies Inc., USA, from Sensotron Inc., USA and from Dow Corning, USA.

These fibers are usually silica fibers or fibers of any other material having a low effective Raman scattering cross section and a low optical absorption in the wavelength range used.

In general, the optical fibers of the device according to the invention comprise individual and separate inlet and outlet ports by which the incident radiation and scattered radiation are transmitted.

The examples which follow are intended to illustrate the process and device according to the invention.

EXAMPLES

The examples below are carried out in a pressure-resistant stainless steel reactor equipped with a stirrer of propeller type and with a baffle. Thermal adjustment is provided by a cryothermostat, which controls the temperature of a gilotherme fluid circulating in a jacket fitted around the reactor. The reactants are introduced by means of membrane volumetric pumps; the flow rate of these reactants is controlled by directing the falling weight of cans placed on balances.

The reaction parameters (reactant flow rates, temperature and pressure) are controlled by an adjusting automaton.

An FT-Raman probe (Ramprobe, Bruker Optik, Germany) is installed facing a window fitted through the jacket of the reactor, at the level of the blades of the stirrer. The window is made of quartz (Infrasil I, Heraeus, Germany).

A rubber seal prevents any stray light from interfering with the signal recorded by the probe and furthermore makes it possible to direct a stream of air in order to retain a temperature lower by 5 to 15° C. than that in the reactor.

The probe is connected to a Fourier transform Raman spectrometer (RFS 100/S, Bruker Optik, Germany) via a first optical fiber (go direction) for transmission of the incident laser irradiation and via a second optical fiber (return direction) for transmission of the Raman scattering.

The spectrometer is connected to a calculator in which the correlation equations and the algorithm for chemometric treatment of the Raman spectra are stored. The concentrations of the reactants (monomers, polymers, water, and the like), determined by virtue of the multivariable chemometric analysis of the Raman spectra of the latex, are transmitted to the control algorithm implanted in the adjusting automaton.

EXAMPLE 1

Development of the Method of In-line Analysis from the Raman Spectra, for the Measurement of the Concentration of Free Monomers and of the Concentration of Polymer Obtained The analytical method is established for a styrene/butadiene/acrylic acid emulsion polymerization reaction.

A. Procedure of the Polymerization

The charges of reactants are shown in the table below.

| Fraction | Ingredients | Mass (g) |
| --- | --- | --- |
| A | Water | 1600 |
|   | Sodium persulfate | 12.1 |
|   | Sodium hydrogen carbonate | 11.5 |
|   | Sodium hydroxide | 10.6 |
|   | Anionic surfactant | 4.5 |
|   | Acrylic acid | 63 |
|   | Butadiene | 117 |
|   | Styrene | 144 |
| B | Styrene | 810 |
|   | Butadiene | 657 |
|   | tert-Dodecyl mercaptan | 18 |
| C | Sodium persulfate | 6.5 |
|   | Water | 150 |

Fraction A is charged, with the exception of the styrene and butadiene, at a temperature of 30° C.; after having purged the reactor with nitrogen, the styrene and butadiene mixture of fraction A is charged and the temperature is brought from 30° C. to 75° C. over 1 h. As soon as the temperature of 75° C. is reached, fraction B is added over 6 h while controlling the temperature of the reactor at 75° C. The medium is maintained at this same temperature for an additional 6 h, during which fraction C is introduced. The reactor is subsequently cooled to ambient temperature and degassed.

B. Analysis of the Polymerization

During the polymerization, samples of latex are withdrawn under pressure every 30 min and analyzed by gravimetry to determine the concentration of polymer Cp and by gas chromatography to determine the residual concentration of monomer Cm.

At the same time, Raman spectra are recorded every 6 min under the following conditions: 200 scans and a resolution of 8 $cm^{-1}$. They are stored in the calculator and then analyzed and compared with the concentrations data obtained off-line.

Chemometric software based on the PLS (Partial Least Squares) method makes it possible to obtain a set of correlation equations used to calibrate the analytical method.

C. Results

Figure 2:
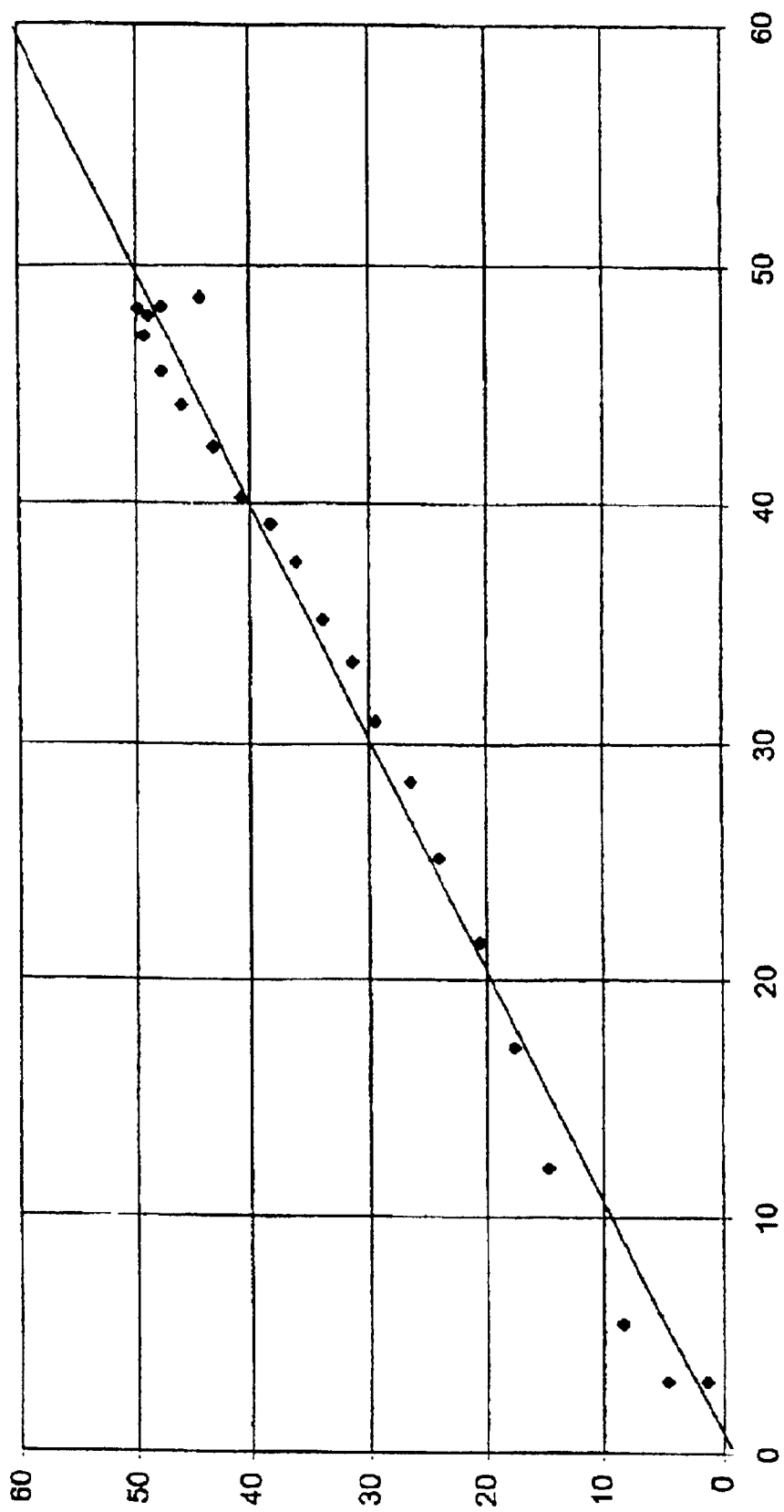
FIG. 2 is a graph showing actual and predicted polymer concentrations during the polymerization in Example 1.

The concentrations of reactants are obtained with accuracy from the Raman spectra obtained, as is illustrated in FIGS. 1 and 2:

FIG. 1 [abscissa: concentration of styrene, measured by off-line chromatography (ppm/mass of latex); ordinate: concentration of styrene, predicted by the calibration (ppm/mass of latex)]

and FIG. 2 [abscissa: concentration of polymer, measured by off-line gravimetry (mass%/mass of latex); ordinate: concentration of polymer, predicted by the calibration (mass%/mass of latex)].

EXAMPLE 2

Validation of the In-line Analytical Methods of Example 1

A. Polymerization

The polymerization carried out in Example 1 is repeated in an identical fashion, except that the level of persulfate is doubled.

B. In-line Analysis of the Polymerization

The Raman spectra recorded every 6 min are treated in-line in the calculator with the correlation equations determined in Example 1, so as to calculate the concentrations of monomer(s) and of polymer. In the same way as in Example 1, samples are withdrawn off-line in order to analyze the concentrations of polymer and of monomer(s).

C. Results

Figure 3:
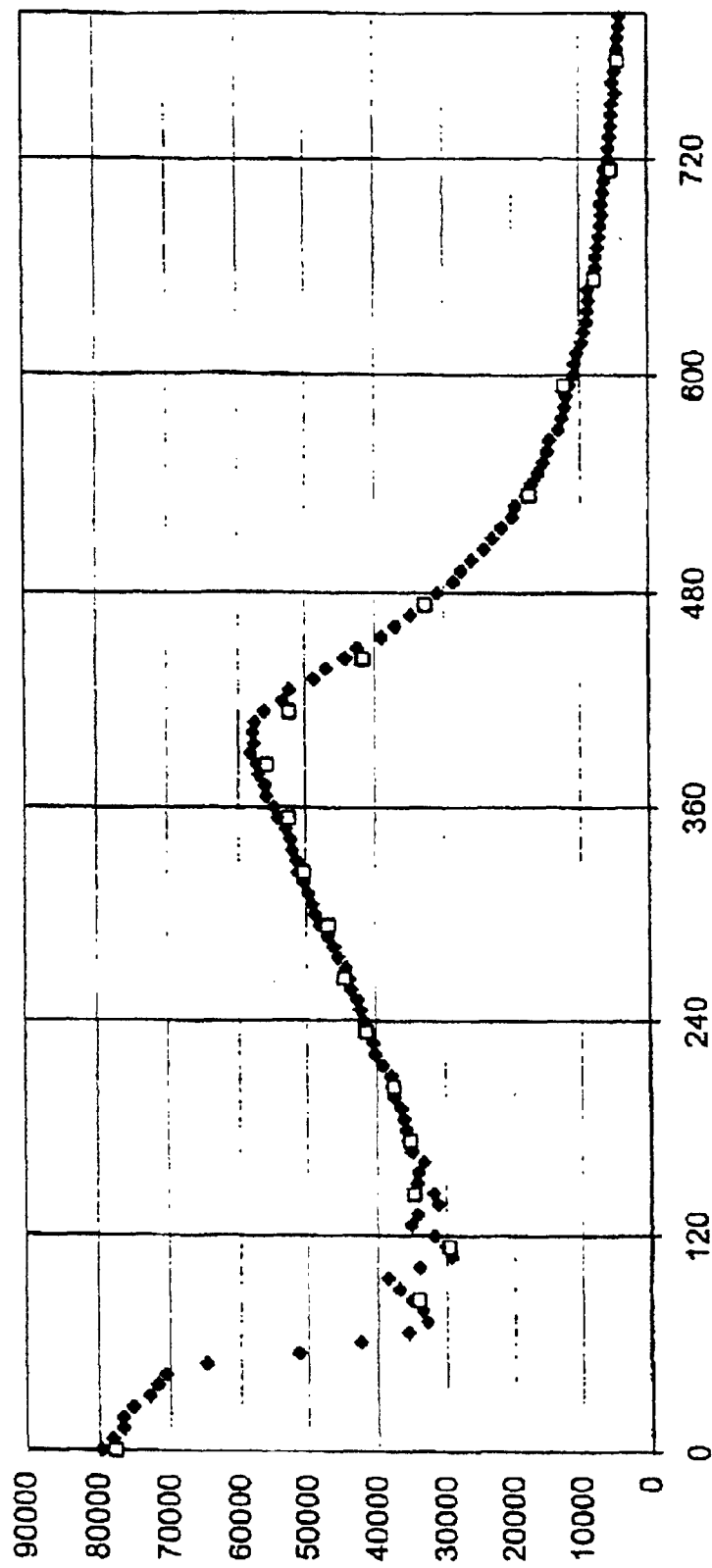
FIG. 3 is a graph showing the actual and predicted concentrations of styrene as a function of time for the polymerization in Example 1.

The concentrations as a function of time are given in FIG. 3 [abscissa: reaction time in min; ordinate: white square: concentration of styrene, measured by off-line gas chromatography (ppm/mass of latex); black diamond: concentration of styrene, predicted by the calibration (ppm/mass of latex)].

This example illustrates the ability of the device to measure the concentration of reactants continuously from the Raman spectra acquired in-line, from the correlation equations established in Example 1.

EXAMPLE 3

Measurement of the Concentration of Free Monomers by the In-line Analytical Method of Example 1

A. Polymerization Procedures

Example 3a:

The charges of reactants are shown in the table below. Fraction A is charged to the reactor at 30° C. The reactor is subsequently purged with nitrogen and its temperature is brought to 85° C. over one hour. Fraction B is then introduced over 260 min and fraction C over 420 min.

Finally, the reactor is cooled to ambient temperature and degassed. The reactor is stirred at a speed of 175 revolutions/min throughout the duration of the trial.

| Fraction | Ingredients | Mass (g) |
|---|---|---|
| A | Water | 1600 |
|   | Latex with a solids content of 30% | 23 |
|   | EDTA | 0.4 |
|   | Acrylic acid | 63 |
| B | Styrene | 1152 |
|   | Butadiene | 576 |
|   | tert-Dodecyl mercaptan | 18 |
| C | Water | 250 |
|   | Sodium persulfate | 18 |
|   | Anionic surfactant | 10 |

Example 3b:

The procedure of Example 3b is identical to that of example 3a with the exception of the stirring speed, which is 225 revolutions/min.

Example 3c:

The procedure of example 3c is identical to that of example 3a with the exception of the stirring speed, which is 275 revolutions/min.

B. Analysis of the Polymerizations (i) For these 3 examples 3a, 3b and 3c, the Raman spectra are recorded and processed in-line every 6 min under the conditions described in example 2, so as to calculate the concentrations of monomer(s) and of polymer.

Figure 4:
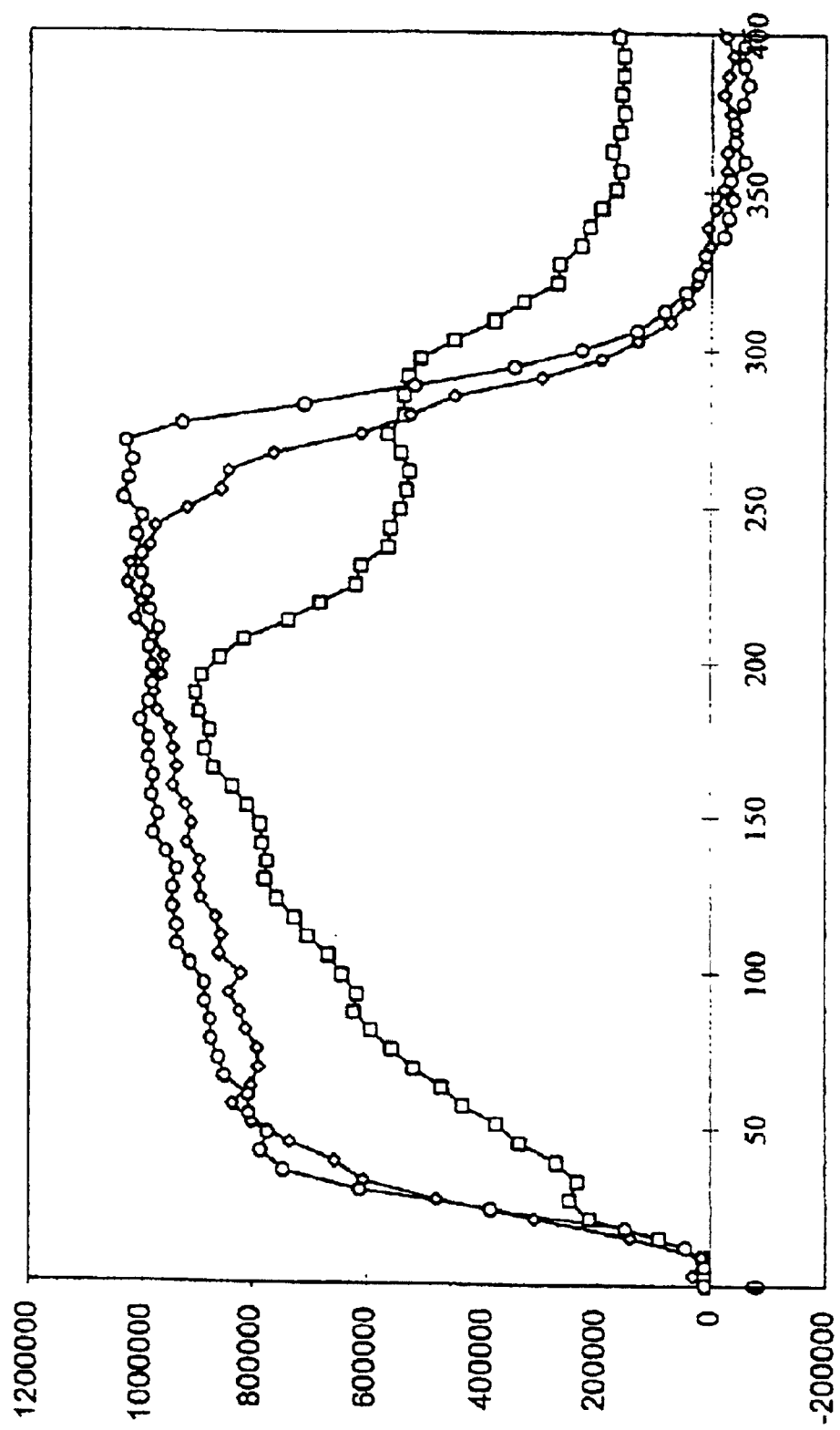
FIG. 4 is a graph showing the concentration of styrene during the polymerization in Examples 3a, 3b and 3c.

The calculations of concentration of styrene with respect to time are given in FIG. 4.

The reaction time in min is on the abscissa. The white squares correspond to the concentrations of styrene in example 3a (ppm/mass of latex); the white diamonds are for the concentrations of styrene in example 3b (ppm/mass of latex); and the white circles represent the concentrations of styrene in example 3c (ppm/mass of latex)].

Figure 5:
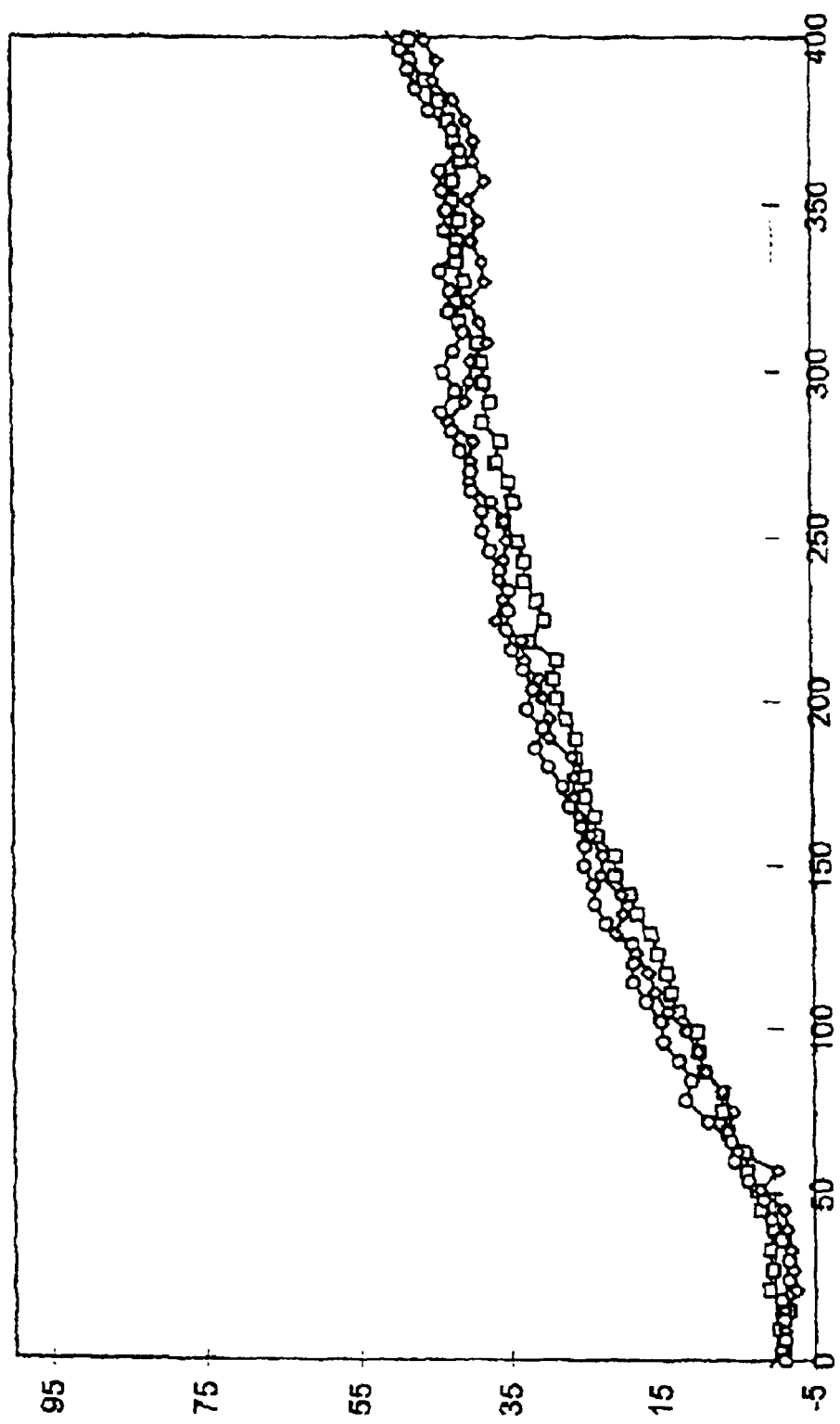
FIG. 5 is a graph showing the concentration of polymer during the polymerization in Examples 3a, 3b and 3c.

The concentration of polymer with respect to time is given in FIG. 5 [abscissa: reaction time in min; ordinate: white square: concentration of polymer in example 3a (mass%/mass: of latex); white diamond: concentration of polymer in example 3b (mass%/mass of latex); white circle: concentration of polymer in Example 3c (mass%/mass of latex)].

(ii) At the same time, the pressure prevailing in the gaseous head space of the reactor is recorded for the 3 examples.

Figure 6:
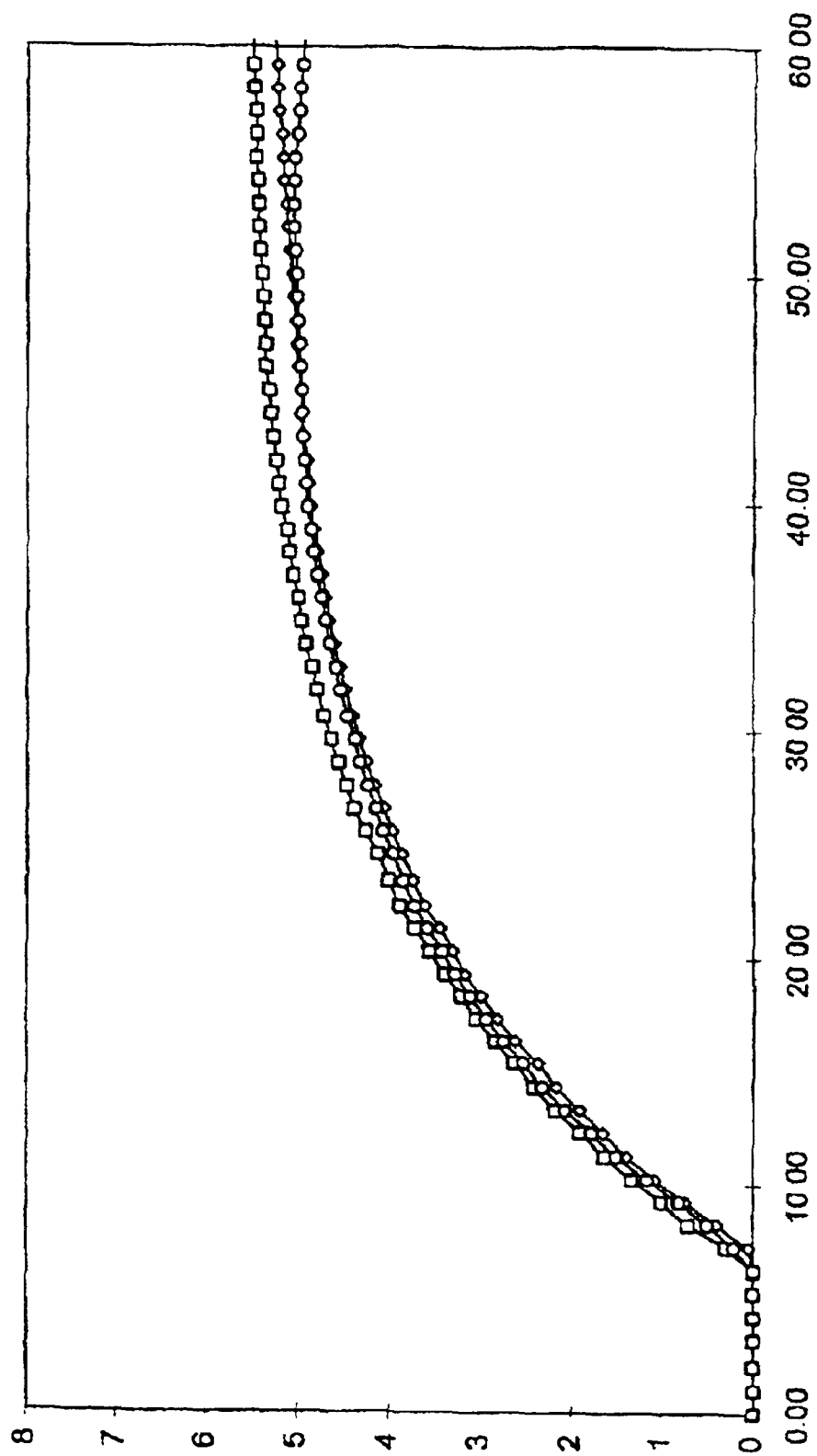
FIG. 6 is a graph showing pressure as a function of time for the polymerization in Examples 3a, 3b and 3c.

The pressures as a function of time are given in FIG. 6 for the first hour of polymerization [abscissa: reaction time in min; ordinate: white square: pressure during example 3a (bar); white diamond: pressure during example 3b (bar); white circle: pressure during example 3c (bar)].

The pressure in the gaseous head space is a qualitative indicator of the progress of the polymerization in the case of styrene/butadiene latices: it increases in proportion as the conversion falls.

C. Results

From FIG. 4, it is observed a priori that, during the first hour, the lower the stirring speed, the lower the concentration of free styrene. This would mean that the instantaneous conversion of the monomers increases in proportion as the stirring speed decreases.

However, this point is completely contradicted by the data in FIG. 6. This is because, in this figure, it is found that the pressure is not lower at the beginning of trial 3a than of trial 3c. The pressures are in fact virtually equivalent: which means that the conversion is therefore not greater during the first hour for example 3a.

This is furthermore confirmed by FIG. 5, in which are represented the variations in the concentration of polymer estimated from the Raman measurement for these same 3 trials, that is to say, the concentration of polymer, and thus also the conversion, is the same during the 3 trials in question.

These three examples thus show that, if the quality of the stirring is insufficient to provide for homogeneity in the reactor (for example, a portion of the monomers can float at the surface of the reaction medium), the correct measurement of the concentration of monomer(s) is not possible. Thus, if only the measurement of the concentration of free monomer(s) is monitored, it is wrongly estimated that the instantaneous conversion is high with respect to the reference data $X_i^0$, which will result in erroneous corrective actions being taken in the event of adjustment. That is to say, the excessively fast or excessively slow introduction of fraction B, which does not make it possible to guarantee the reproducibility of the process and the final quality of the latex.

EXAMPLE 4

Measurement of the Concentration of Polymer Obtained by the In-line Analytical Method of Example 1

A. Polymerization Procedures

Example 4a:

The polymerization procedure is identical to that of example 1.

Example 4b:

The polymerization procedure is identical to that of example 1. However, the pump which has to introduce fraction B, did not operate correctly during part of the polymerization (uneven flow rate).

Figure 7:
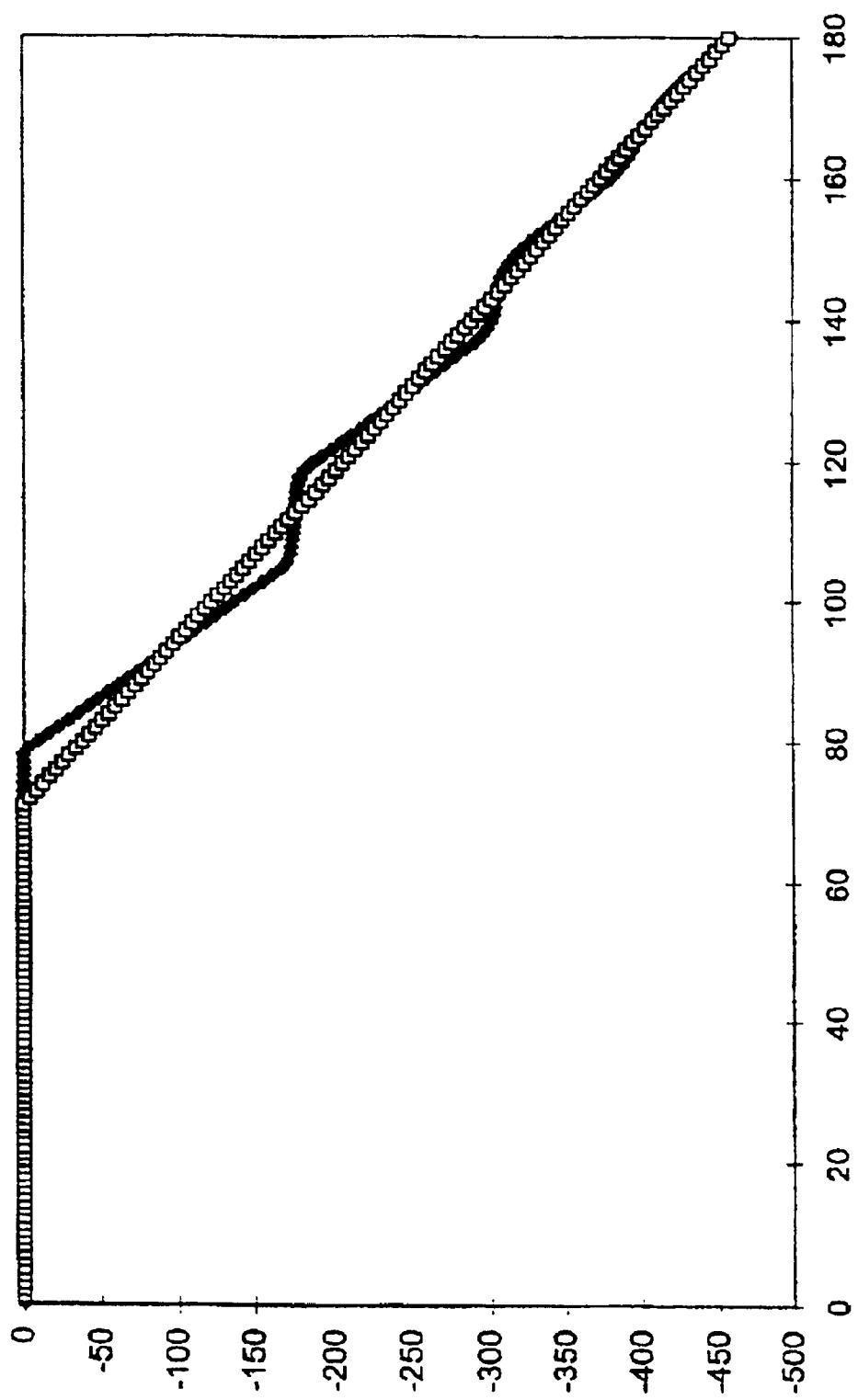
FIG. 7 is a graph showing the difference in the behavior of the pump used to introduce fraction B in Examples 4a and 4b.

The difference in behavior of the pump is observed in FIG. 7 [abscissa: time (min); ordinate: white square: loss in weight (g) of the can containing fraction B during example 4a; black diamond: loss in weight (g) of the can containing fraction B during example 4b. The loss in weight is steady in the case of example 4a, whereas oscillations are visible in the case of example 4b.

B. Analysis of the Polymerizations

The Raman spectra recorded every 6 min are processed in-line in the calculator with the correlation equations determined in example 1, so as to calculate the concentrations of monomer(s) and of polymer.

Figure 8:
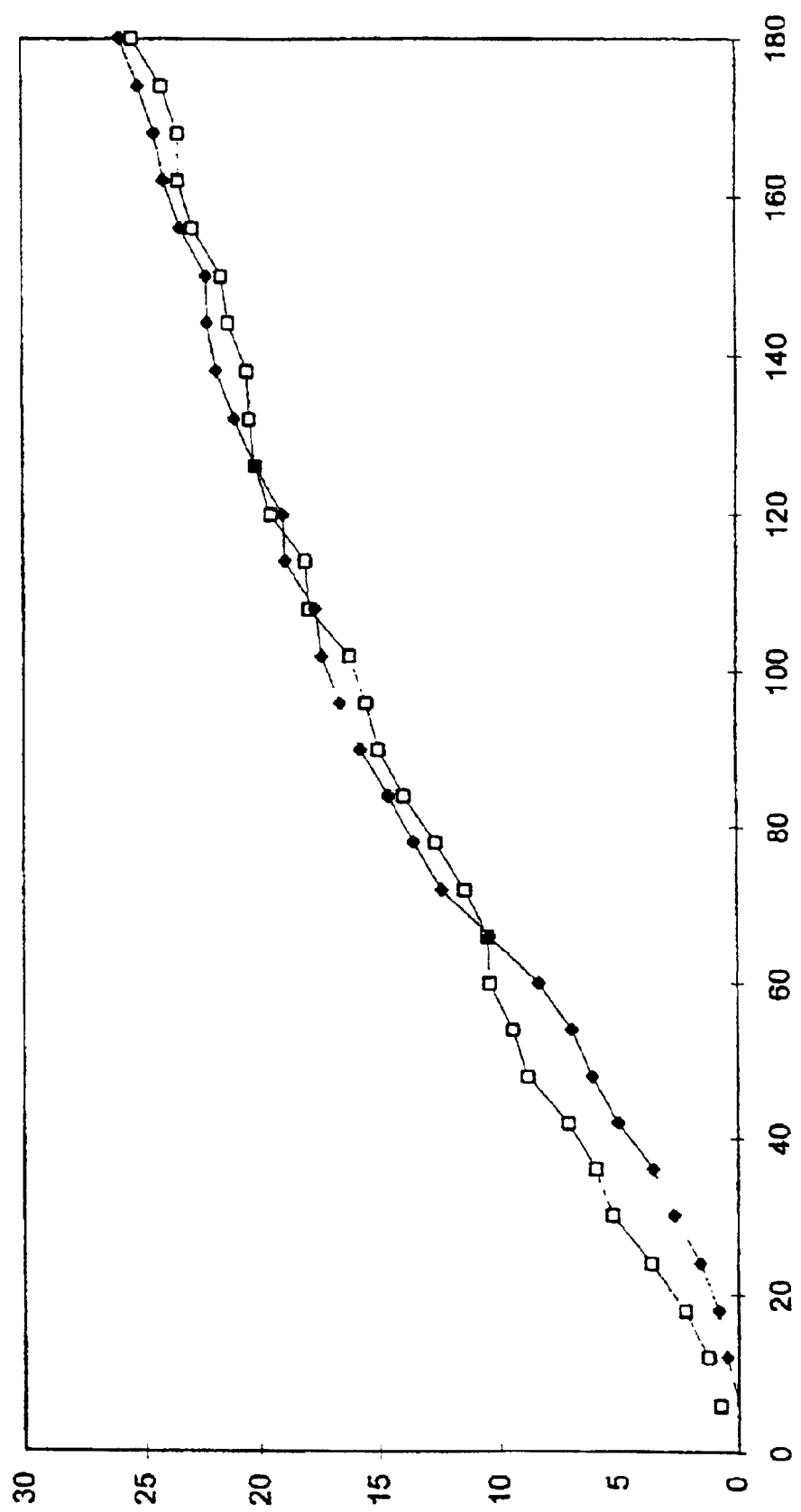
FIG. 8 is a graph showing the concentration of polymer as a function of time for Examples 4a and 4b.

The calculations of the concentration of polymer as a function of time are given in FIG. 8 [abscissa: reaction time (min); ordinate: white square: concentration of polymer for example 4a (mass%/latex); black diamond: concentration of polymer for example 4b (mass%/latex)].

Figure 9:
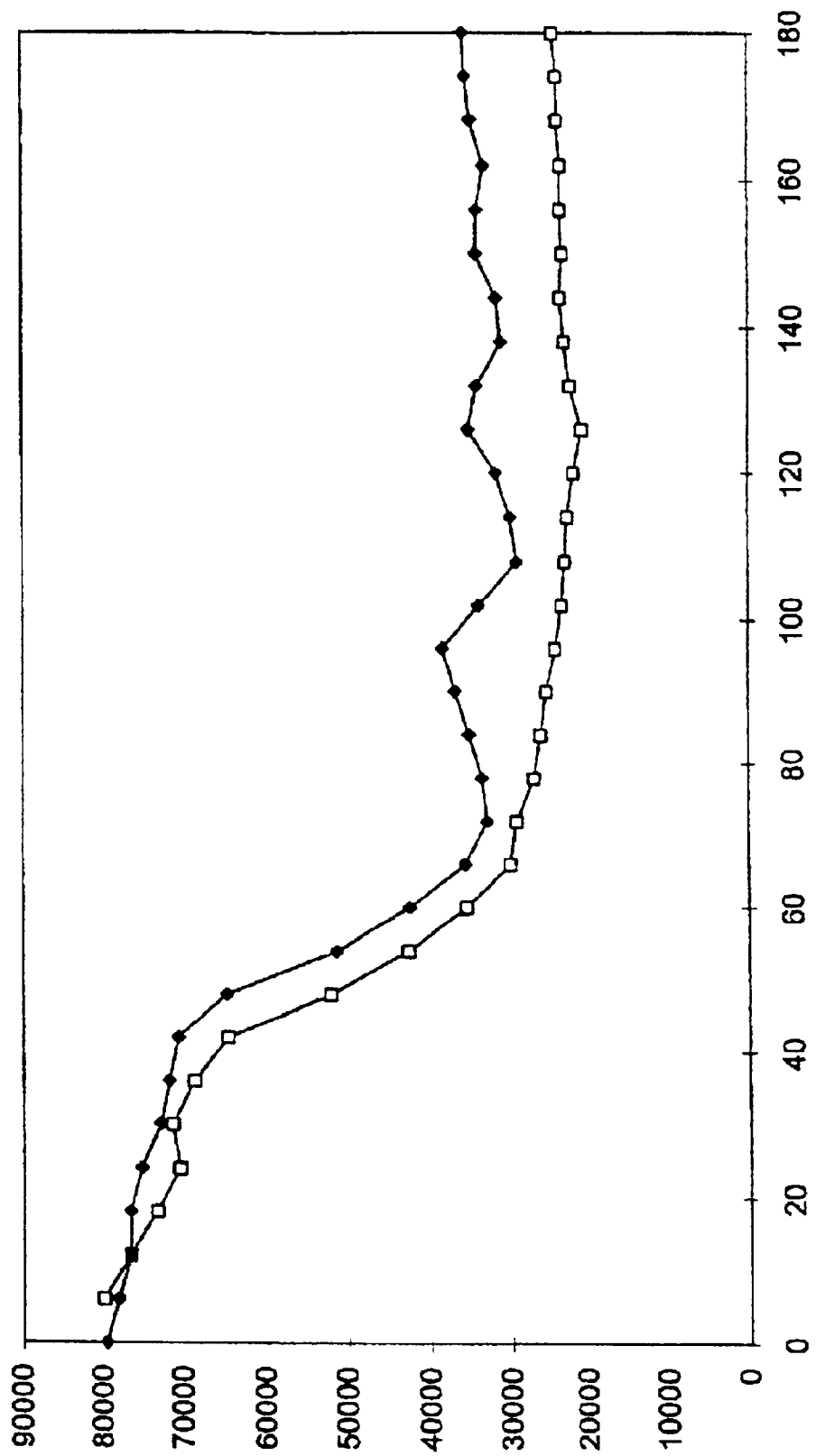
FIG. 9 is a graph showing the concentration of styrene as a function of time for Examples 4a and 4b.

The calculations of concentration of styrene as a function of time are given in FIG. 9 [abscissa: reaction time (min); ordinate: white square: concentration of styrene during example 4a (ppm/latex); black diamond: concentration of styrene during example 4b (ppm/latex)].

C. Results

The curves of example 4a and of example 4b are superimposed in FIG. 8.

The in-line measurement of the concentration of polymer in the latex thus does not reveal the difference in the procedures of examples 4a and 4b (operation of the pump).

This measurement does not make it possible to anticipate the necessary corrections which make it possible to obtain identical latices in examples 4a and 4b. It can thus with difficulty by itself alone instantaneously report transitory events, such as inadequate temporary operation of a feed pump.

This example shows that the single in-line measurement of the concentration of polymer does not make it possible to guarantee the reproducibility of the process and the final quality of the latex.

EXAMPLE 5

Simultaneous Measurement of the Concentration of Free Monomers and Polymer Obtained According to the Method of Example 1

A series of experiments, 5-1 to 5-10, is carried out by reproducing the polymerization procedure of example 1.

The in-line analysis of the concentration of monomer and of polymer is carried out under identical conditions to those of examples 2. The process data Xi (instantaneous conversion) and Xc (cumulative conversion) defined above, calculated from the concentrations Cm and Cp measured simultaneously in-line, are plotted in the curve Xi=f(Xc) form. 10 curves corresponding to the 10 polymerization trials are thus obtained. The 10 curves differ by the experimental variability inherent to the process. The aim is to establish a confidence band around the reference curve from these 10 trials, which will be known as the dispersion index (DI). The procedure for this is as follows: the reference curve is calculated by adjustment from the 10 experimental curves Xi=f(Xc) of trials 5-1 to 5-10; it is thus a mean "reference" curve $Xi^0 = f(Xc^0)$ The confidence band is constructed by calculating beforehand an estimation of the pure error from all the experimental results by applying the methodology described in the following work: Draper N. R., Smith H., Applied Regression Analysis, Second Edition, Wiley, 1981.

The upper and lower limits of the simultaneous confidence band for the reference curve are thus calculated. The confidence level chosen is 99% (in other words, during polymerization, the value of the process data at the instant under consideration lies within the confidence band, which means that the probability that the progress of the polymerization is not significantly different from that corresponding to the reference curve is greater than 0.99).

The dispersion index (DI) is the area of the confidence band calculated over the range defined by an abscissa (Xc) varying from 0 to 1 and an ordinate (Xi) varying from 0 to 1. This crude value is multiplied by 1 000. The smaller the value of the DI, the less the process is dispersed and consequently the greater is the reproducibility and thus the reliability of this process. The calculations were carried out with the SAS/STAT and SAS/IML modules of the SAS software, version 6.12 (SAS Institute, USA). The results are given in the table below.

EXAMPLE 6

Process According to the Invention

Simultaneous In-line Measurement of the Concentration of Free Monomers and Polymer Obtained According to the Method of Example 1 and In-line Adjustment The series of trials 6-11 to 6-20 is carried out in an identical way to the series of example 5. However, fraction B is no longer introduced according to a predetermined profile; this is because a control algorithm is programed in the adjusting automaton to guide the feeding of the monomers of fraction B so as to minimize the error between the curve Xi=f(Xc) and the preset curve $Xi^0=f(Xc^0)$.

The control algorithm is based on adjustment of PID type ("proportional integral differential adjustment"). In the same way as for the series of trials 5-1 to 5-10, the statistical method presented above is used to calculate the confidence band over the trials and to reduce therefrom the dispersion index (DI). The results are given; in the table below:

| Reference of the trials | Dispersion index (DI) |
|---|---|
| 5–1 to 5–10 (without in-line adjustment) | 87 |
| 6–11 to 6–20 (with in-line adjustment) | 50 |

Comparison of the series of trials of example 5 and of the series of trials of example 6 reveals a much lower dispersion index (DI) when the polymerization is carried out with in-line control rendered possible by virtue of the in-line FT-Raman analysis: the novel process forming the subject matter of the invention is thus much more reproducible and, for this reason, guarantees a consistent level of performance.

What is claimed is:

1. A process for the preparation of a latex with predefined properties by emulsion (co)polymerization of at least one ethylenically unsaturated monomer, wherein the process is carried out with continuous in situ monitoring of the (co) polymerization comprising the following stages:
   (i) emitting incident light radiation within the spectral band situated between 200 nm and 1 400 nm, into the emulsion,
   (ii) picking up the light scattered by the reaction medium and transmitting it to a Raman spectrometer,
   (iii) determining the Raman spectrum, which shows the energy of the scattered light as a function of the difference in wavelength with respect to the incident light radiation,
   (iv)
   a) by either the intensities (areas or heights) of specific lines of the spectrum:
      of un(co)polymerized free monomer(s) in the reaction medium,
      and of the polymer obtained,
   b) or the concentrations of un(co)polymerized free monomer(s) in the reaction medium and of the polymer obtained are calculated from the Raman spectrum using quantitative spectral analytical methods;
   (v) calculating the process data either from the concentrations of free monomer(s) and of the polymer obtained or from the intensities (areas or heights) of specific lines of the spectrum of free monomer(s) in the reaction medium and from the intensities (areas or heights) of specific lines of the spectrum of the polymer obtained;
   (vi) comparing these process data with reference data specific to the process for the production of the latex with the predefined properties;
   (vii) and adjusting the reaction parameters, comprising the pressure, the stirring of the medium and the feeding with monomers, in order to minimize the difference between the process data measured in-line and the reference process data.

2. The process as claimed in claim 1, wherein the Raman spectrometer is a Fourier transform or optical dispersive Raman spectrometer.

3. The process as claimed in claim 2, wherein the latex results from the emulsion (co)polymerization of ethylenically unsaturated monomers selected from the group consisting of:

styrene, α-methylstyrene or vinyltoluene;

dienes;

(meth)acrylic esters comprising esters of acrylic acid and of methacrylic acid with hydrogenated or fluorinated C1–C12;

vinyl nitrites having from 3 to 12 carbon atoms;

carboxylic acid vinyl esters;

vinyl halides;

and their mixture.

4. The process as claimed in claim 3, wherein the emulsion additionally comprises other ethylenically unsaturated monomers, (co)polymerizable with the monomers of the preceding claim, selected from the group consisting of:

unsaturated ethylenic mono- and dicarboxylic acids;

monoalkyl esters of the abovementioned dicarboxylic acids with alkanols and their N-substituted derivatives;

amides of unsaturated carboxylic acids;

ethylenic monomers comprising a sulfonic acid group and its alkali metal or ammonium salts;

unsaturated ethylenic monomers comprising a secondary, tertiary or quaternary amino group or a heterocyclic group comprising nitrogen;

zwitterionic monomers;

and their mixture.

5. The process as claimed in claim 4, wherein the direct in-line monitoring is carried out continuously for the preparation of styrene/butadiene latex by the aqueous emulsion (co)polymerization of styrene with butadiene.

6. The process as claimed in claim 1, wherein the direct in-line monitoring is carried out for the preparation of a latex by emulsion (co)polymerization in which the continuous phase is composed of water.

7. The process as claimed in claim 1, wherein the intensity (area or height) of the specific lines of the Raman scattering spectrum is calculated:

on the one hand, at approximately $1\,635 \pm 100$ cm$-1$, a line associated with the stretching vibration of the carbon-carbon double bond of the free monomers which have not yet (co)polymerized, and, on the other hand, at approximately $1\,660 \pm 100$ cm$-1$, a line associated with the stretching vibrations of the carbon-carbon double bonds incorporated in the main chain of the polymer obtained when the monomer mixture comprises at least one diene compound.

8. The process as claimed in claim 1, wherein the direct in-line monitoring is carried out by calculating the concentrations of free monomer(s) and of the polymer obtained by multivariable chemometric analytical methods, this calculation being made by a computer having in memory equations establishing a correlation between the Raman spectra and the concentrations of free monomer(s) and of the polymer obtained and the measured Raman spectra being introduced into said memory in order to calculate the concentrations of free monomer(s) and of the polymer obtained during the polymerization.

* * * * *